(12) United States Patent
Shirakawa et al.

(10) Patent No.: US 8,120,791 B2
(45) Date of Patent: Feb. 21, 2012

(54) IMAGE SYNTHESIZING APPARATUS

(75) Inventors: Masanobu Shirakawa, Nagano (JP); Shuji Tsuji, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 12/494,820

(22) Filed: Jun. 30, 2009

(65) Prior Publication Data

US 2009/0262219 A1    Oct. 22, 2009

Related U.S. Application Data (63) Continuation of application No. 10/965,858, filed on Oct. 18, 2004, now Pat. No. 7,573,601.

(51) Int. Cl.
| | |
|---|---|
| *G06F 3/12* | (2006.01) |
| *G06K 15/00* | (2006.01) |
| *G06K 9/64* | (2006.01) |
| *H04N 1/60* | (2006.01) |
| *H04N 5/262* | (2006.01) |

(52) U.S. Cl. ............. 358/1.13; 358/1.15; 358/1.16; 358/1.9; 382/278; 348/218.1; 348/220.1; 348/239

(58) Field of Classification Search ............. 358/1.15, 358/1.16, 1.9, 1.13, 1.18, 538, 540, 453, 358/302; 382/278; 348/218.1, 220.1, 239 348/584, 586
See application file for complete search history.

(56) References Cited

U.S. PATENT DOCUMENTS

| | | | |
|---|---|---|---|
| 4,456,931 A | 6/1984 | Toyoda et al. | |
| 4,641,255 A | 2/1987 | Hohmann | |
| 5,077,610 A | 12/1991 | Searby et al. | |
| 5,506,946 A | 4/1996 | Bar et al. | |
| 5,583,536 A | 12/1996 | Cahill, III | |
| 5,623,587 A | 4/1997 | Bulman | |
| 5,845,166 A | 12/1998 | Fellegara et al. | |
| 5,914,748 A | 6/1999 | Parulski et al. | |
| 5,978,016 A | 11/1999 | Lourette et al. | |
| 6,141,063 A | 10/2000 | Gehrmann | |
| 6,195,513 B1 | 2/2001 | Nihei et al. | |
| 6,343,987 B2 | 2/2002 | Hayama et al. | |
| 6,441,811 B1 | 8/2002 | Sawada et al. | |
| 6,441,854 B2 | 8/2002 | Fellegara et al. | |

(Continued)

FOREIGN PATENT DOCUMENTS

CN    1212102 A    12/2007

(Continued)

OTHER PUBLICATIONS

International Search Report dated Aug. 5, 2003.

(Continued)

*Primary Examiner* — Thomas Lett (74) *Attorney, Agent, or Firm* — Sughrue Mion, PLLC (57) ABSTRACT

There are provided a framing assisting means for displaying as a moving picture object data as well as a profile of an area that is synthesized with a foreground of selected background data on an LCD 26 in a first magnification, a recording means for storing the object data selected by a shutter instruction in a nonvolatile memory to correlate with the selected background data, and a playing means for displaying as a still picture the object data stored in the nonvolatile memory and the background data correlated with the object data on the LCD 26 by applying a magnification varying process that is used to display the object data on the LCD 26 in a magnification smaller than the first magnification.

9 Claims, 9 Drawing Sheets

U.S. PATENT DOCUMENTS

| | | | |
|---|---|---|---|
| 6,556,243 | B1 | 4/2003 | Dotsubo et al. |
| 6,556,775 | B1* | 4/2003 | Shimada ............... 386/121 |
| 6,738,059 | B1 | 5/2004 | Yoshinaga et al. |
| 6,847,388 | B2 | 1/2005 | Anderson |
| 6,867,801 | B1 | 3/2005 | Akasawa et al. |
| 6,964,537 | B1 | 11/2005 | Ong |
| 6,987,535 | B1 | 1/2006 | Matsugu et al. |
| 7,057,650 | B1* | 6/2006 | Sakamoto ............... 348/239 |
| 7,057,658 | B1 | 6/2006 | Shioji et al. |
| 7,079,706 | B2 | 7/2006 | Peterson |
| 7,088,396 | B2 | 8/2006 | Fredlund et al. |
| 7,164,441 | B1 | 1/2007 | Miyazaki et al. |
| 7,221,395 | B2 | 5/2007 | Kinjo |
| 7,342,486 | B2 | 3/2008 | Tsukada et al. |
| 7,471,312 | B2 | 12/2008 | Toyoda |
| 2002/0080251 | A1 | 6/2002 | Moriwaki |
| 2002/0090910 | A1 | 7/2002 | Takemura |
| 2002/0097327 | A1* | 7/2002 | Yamasaki ............... 348/239 |
| 2002/0140829 | A1 | 10/2002 | Colavin et al. |
| 2002/0176636 | A1 | 11/2002 | Shefi |
| 2003/0026609 | A1 | 2/2003 | Parulski |
| 2004/0141070 | A1 | 7/2004 | Chiku et al. |
| 2004/0173686 | A1 | 9/2004 | Al Amri |
| 2005/0016702 | A1 | 1/2005 | Ash et al. |
| 2005/0259173 | A1 | 11/2005 | Nakajima et al. |
| 2006/0125924 | A1 | 6/2006 | Ing-Song et al. |
| 2007/0019072 | A1 | 1/2007 | Bengtsson et al. |

FOREIGN PATENT DOCUMENTS

| | | | |
|---|---|---|---|
| DE | 19814409 | A1 | 10/1998 |
| EP | 0647057 | A1 | 4/1995 |
| EP | 0675648 | A2 | 10/1995 |
| EP | 0837428 | A2 | 4/1998 |
| EP | 0944248 | A2 | 9/1999 |
| EP | 1100262 | A1 | 5/2001 |
| JP | 10164498 | A | 6/1998 |
| JP | 10271427 | A | 10/1998 |
| JP | 11-8818 | A | 1/1999 |
| JP | 11004403 | A | 1/1999 |
| JP | 11008831 | A | 1/1999 |
| JP | 11168689 | A | 6/1999 |
| JP | 11187314 | A | 7/1999 |
| JP | 11196362 | A | 7/1999 |
| JP | 11-234506 | A | 8/1999 |
| JP | 11298764 | A | 10/1999 |
| JP | 2000307941 | A | 11/2000 |
| JP | 2000350086 | A | 12/2000 |
| JP | 2000358206 | A | 12/2000 |
| JP | 2001024927 | A | 1/2001 |
| JP | 200145352 | A | 2/2001 |
| JP | 2001045352 | A | 2/2001 |
| JP | 2001127986 | A | 5/2001 |
| JP | 2001177764 | A | 6/2001 |
| JP | 2001285420 | A | 10/2001 |
| JP | 2002044416 | A | 2/2002 |
| JP | 2002158922 | A | 5/2002 |
| WO | 9830020 | A1 | 7/1998 |

OTHER PUBLICATIONS

European Search Report dated Aug. 3, 2006.
Supplemental European Search Report dated Feb. 25, 2008.
US Office Action issued for U.S. Appl. No. 11/003,783, dated Jan. 7, 2010.
Non-Final Office Action dated Sep. 19, 2011, in related U.S. Appl. No. 11/003,783.

* cited by examiner

LAYOUT INFORMATION

PLAY SIZE: POSTCARD
BACKGROUND ALLOCATION AREA:
    UPPER LEFT COORDINATES (x,y),
    LOWER RIGHT COORDINATES (x,y)
OBJECT ALLOCATION AREA:
    UPPER LEFT COORDINATES (x,y),
    LOWER RIGHT COORDINATES (x,y)

IMAGE SYNTHESIZING APPARATUS

This is a continuation of application Ser. No. 10/965,858 filed Oct. 18, 2004. The entire disclosure of the prior application, application Ser. No. 10/965,858 is considered part of the disclosure of the accompanying continuation application and is hereby incorporated by reference.

TECHNICAL FIELD

The present invention relates to a digital camera.

BACKGROUND ART

The digital camera has the use of recording the data as material of composite image, for example. The composite image is used widely to print a photograph with the comment, a framed photograph seal, and so on. In the event that a frame image is printed so as to overlap with an object, etc., in some case a part of the object is trimmed by the composite process. In such case, if background data for composite are stored previously in the memory and then an area of the object that is synthesized with the background data and printed actually is displayed on an electronic view finder in shooting, it can be facilitated to record the object in an appropriate composition.

In JP-A-2001-45352, there is disclosed the digital camera that displays composite image data obtained by synthesizing the data representing the background and the data representing the object on a liquid crystal panel and then records such data in an external memory after the shooting.

In JP-A-2000-358206, there is disclosed the digital camera that records the data representing the object and the data setting a printing range used to print the data in conformity with an identification photograph, or the like, etc. in a memory so as to correlate them mutually and then displays the object image together with a frame indicating a trimmed area in printing as a moving picture on an external display.

As disclosed in above JP-A-2001-45352, the display of the composite image data, which is obtained by synthesizing the data representing the background and the data representing the object on the electronic view finder, makes it possible for the operator to check the result of the composite image.

Meanwhile, in the image composite process, in some cases the photographic image of the object should be allocated not to the overall composite image but to a part of such image, for example, the case that a New Year's card obtained by synthesizing the photographic image of the object recorded by the digital camera and the background data to allocate the photographic image to an almost half area should be printed, and so forth. In the conventional art, the method of controlling the electronic view finder suitable for the photographic image data used in the composite process, in which the photographic image of the object should be allocated not to the overall composite image but to a part of such image, has not been proposed.

It is an object of the present invention to provide a digital camera, capable of making it easy to record image data used in a composite process in an adequate composition and also making it easy to grasp a play image of composite image while viewing image data used in the composite process in which a photographic image of the object is allocated not to the overall composite image but to a part of such image.

DISCLOSURE OF THE INVENTION

In order to achieve the above object, a digital camera according to the present invention for accepting a shutter instruction when object data representing an object image as well as a profile of an area that is synthesized with a foreground of background data is being displayed as a moving picture on a display in a first magnification, comprises a synthesizing means for synthesizing the object data and the background data; and a playing means for displaying as a still picture an entirety of composite image data obtained by synthesizing the object data and the background data on one screen of the display by applying a magnification varying process that is used to display the object data on the display in a magnification smaller than the first magnification. In this case, the magnification mentioned herein is a value indicating a ratio of the number of pixels derived after the process to the number of pixels derived before the process when an interpolation process or a thinning process is applied to the image data in response to the number of pixels in the display area.

Also, in order to achieve the above object, a digital camera according to the present invention, comprises an image processing means for forming object data representing an object image based on an output of an image sensor; a setting means for setting background data that is synthesized with the object data; a framing assisting means for displaying as a moving picture the object data as well as a profile of an area that is synthesized with a foreground of the background data set by the setting means on a display in a first magnification; a recording means for storing the object data selected by a shutter instruction in a nonvolatile memory to correlate with the background data set by the setting means; and a playing means for displaying as a still picture an entirety of composite image data obtained by synthesizing the object data stored in the nonvolatile memory and the background data correlated with the object data on one screen of the display by applying a magnification varying process that is used to display the object data on the display in a magnification smaller than the first magnification.

At the time of shooting, it becomes easy to record the object image in an adequate composition since a profile of the area that is synthesized with the foreground of the background data is displayed while displaying moving picture data of the object image as large as possible. Also, at the time of checking the play image, it becomes easy to grasp a played state of the image since an entirety of the played image is displayed within one screen. As a result, since the digital camera according to the present invention varies the magnification applied to display the object data when the object image is displayed as a moving picture in the shooting and when the composite image is displayed as a still picture after the shooting, it is made easy to record the image data used in the composite process in the adequate composition and also it is made easy to grasp the play image of composite image while viewing image data used in the composite process in which a photographic image of the object is allocated not to the overall composite image but to a part of such image.

In addition, in the digital camera according to the present invention, the framing assisting means synthesizes the background data with the foreground of the object data and displays resultant data. Therefore, it is made easy to harmonize the object image and the background data image.

Further, in the digital camera according to the present invention, the magnification varying process is a programmed process. Therefore, increase in a production cost caused by varying a display magnification can be suppressed.

Furthermore, if the magnification varying process used to display the object data on the display in a magnification smaller than the first magnification is provided as the programmed process and also the high-speed processing is executed by using mainly the hardware when the object data is to be displayed on the display in the first magnification, smooth displaying of the moving picture can be achieved while suppressing increase in a production cost.

In this case, respective functions of a plurality of means provided to the present invention can be implemented by the hardware resource whose function is identified by the configuration itself, the hardware resource whose function is identified by the program, or their combination. Also, respective functions of a plurality of means are not limited to those implemented by the hardware resources each of which is physically and mutually independent.

Moreover, the present invention can be identified not only as the invention of the device but also as the invention of the program, the invention of a recording medium for recording the program, or the invention of a method.

BEST MODE FOR CARRYING OUT THE INVENTION

An embodiment of the present invention will be explained with reference to particular examples hereinafter.

Figure 2:
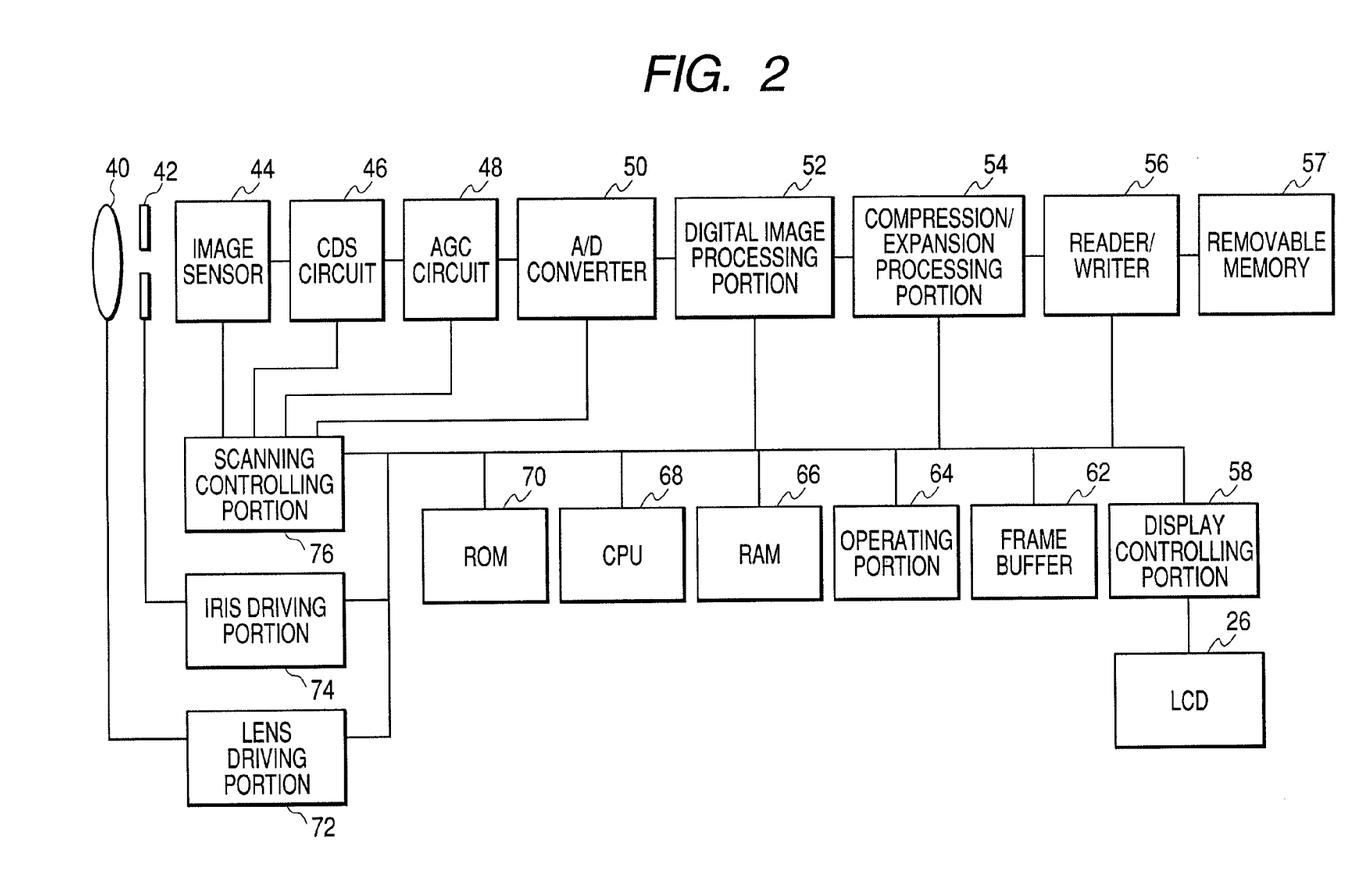
FIG. 2 is a block diagram showing the digital camera according to the embodiment of the present invention.
Figure 3A:
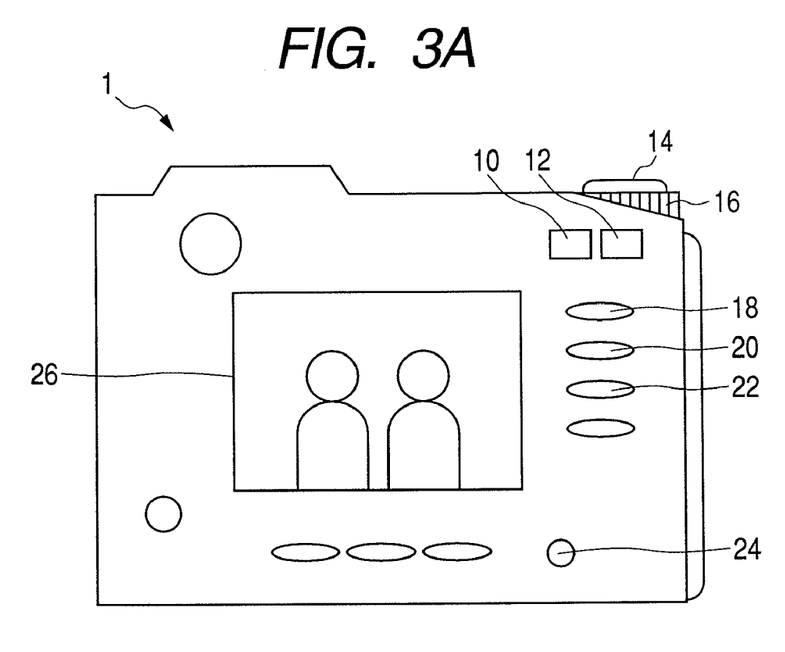
FIG. 3(A) is a rear view of the digital camera according to the embodiment of the present invention.
Figure 3B:
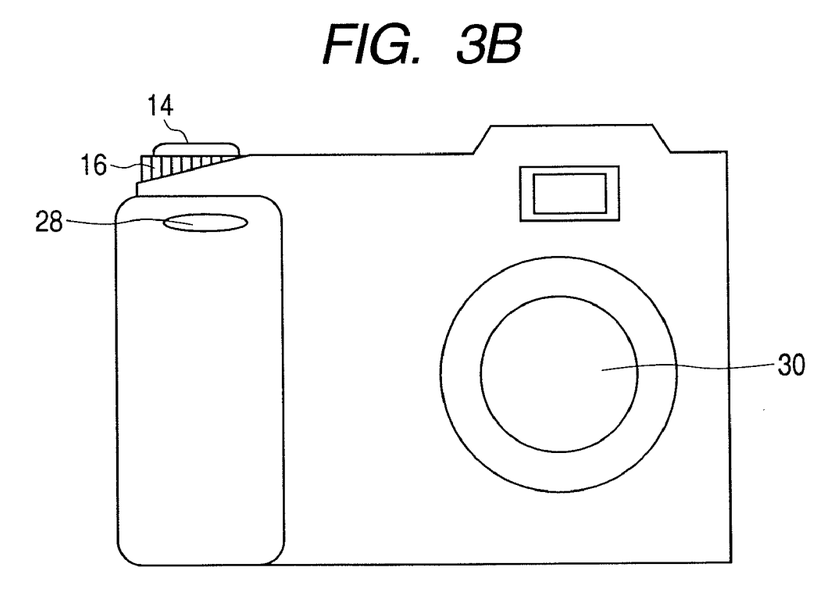
FIG. 3(B) is a front view of the same.

FIG. 2 is a block diagram showing a configuration of a digital camera 1 according to an embodiment of the present invention. FIG. 3(A) and FIG. 3(B) are a front view and a rear view showing an external appearance of the digital camera 1 respectively.

A lens driving portion 72 drives a lens 40 such that an image of the object is formed on a light receiving portion of an image sensor 44 in a magnification that responds to a signal input from a CPU 68. An iris driving portion 74 drives an optical iris in such a way that a quantity of incident light incident upon the image sensor 44 is set to a quantity of incident light that responds to a signal input from the CPU 68.

The image sensor 44 is an area image sensor on which a color filter array composed of four complementary color filters of C (Cyan), M (Magenta), Y (Yellow), and G (Green) is on-chip formed, and stores charges obtained by photoelectrically converting the received light for a predetermined time and then outputs an electric signal in response to a quantity of received light every photoelectric converting element. In this case, the color filter array may be composed of complementary color filters of three colors CMY, or may be composed of primary color filters of R (Red), G (Green), and B (Blue).

A CDS circuit 46 executes a process of reducing the noise contained in an analog electric signal. An AGC circuit 48 adjusts a level of the analog electric signal by gain adjustment. An A/D converter 50 quantizes the analog electric signal being subjected to above respective processes into a digital signal with a predetermined tone. A scanning controlling portion 76 outputs a shift pulse, a vertical transfer pulse, a horizontal transfer pulse, etc. to the image sensor 44, and outputs a drive pulse to the CDS circuit 46, the AGC circuit 48, and the A/D converter 50 to operate them in synchronism with the image sensor 44.

A digital image processing portion 52 is composed of a DSP (Digital Signal Processor), for example, and executes image generating process, white balance correction, gamma correction, color space conversion, etc. based on the image signal output from the A/D converter 50, and forms object data representing R, G, B tone values, Y, Cb, and Cr tone values, etc., for example, every pixel, and stores resultant data in a RAM 66. In this case, the image generating process mentioned herein is mainly the process that generates the image data having four tone values of CMYG every pixel by means of the interpolation process using the digital data representing any tone value of CMYG corresponding to an output of each photoelectric converting element.

A compression/expansion processing portion 54 compresses the object data being output from the digital image processing portion 52 to form compressed image data based on JPEG format, for example, in a shooting mode, and expands the compressed image data being read from a removable memory 57 by using a reader/writer 56 and stores resultant data in a RAM 66 in a play mode. The removable memory 57 composed of a nonvolatile memory such as a flash memory, or the like can be detachably attached to the reader/writer 56. The reader/writer 56 writes data into the removable memory 57, and reads the data stored in the removable memory 57.

An operating portion 64 includes various buttons such as a power supply button 14 for turning ON/OFF a power supply, a dial switch 16 used to set modes such as a shooting mode, a play mode, a direct print mode, etc., a shutter button 28 used to input a shutter instruction, a background setting button 18 used to set the background in the shooting mode, zoom lenses 10, 12 used to set a magnification of a zoom lens, a select next key 20, a select previous key 22, a decision key 24, etc. and a circuit for sensing the pushing of the buttons and a rotation angle of the dial switch 16.

A display controlling portion 58 executes a process of thinning the image data stored in the RAM 66 in a fixed magnification in response to a display area of the display, a color space converting process, a composite process, etc., and drives an LCD (Liquid Crystal Display) 26 as a display based on the display data that are formed by applying these processes. A background area and a foreground area for storing individually the image data to be synthesized are provided to a frame buffer 62. The display controlling portion 58 has a synthesis processing circuit that displays the composite image on the LCD 26 by displaying pixels of the image data stored in the background area in preference to transparent pixels of the image data stored in the foreground area and displaying opaque pixels of the image data stored in the foreground area in preference to the pixels of the image data stored in the background area.

The CPU 68 controls the overall digital camera 1 by executing a computer program stored in a ROM 70. The ROM 70 is a memory that stores the computer program used to execute various controls by the CPU 68, and soon. The RAM 66 is a memory that stores temporarily various programs and data.

With the above, the configuration of the digital camera 1 is explained. Next, background data will be explained hereunder.

Figure 4A:
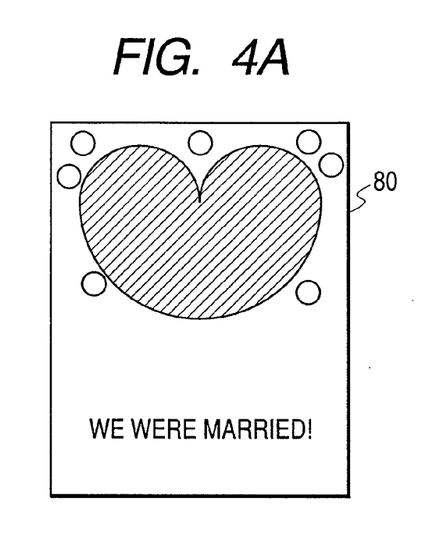
FIG. 4 is a schematic view showing background data and layout information stored in a removable memory in the embodiment of the present invention.
Figure 4B:
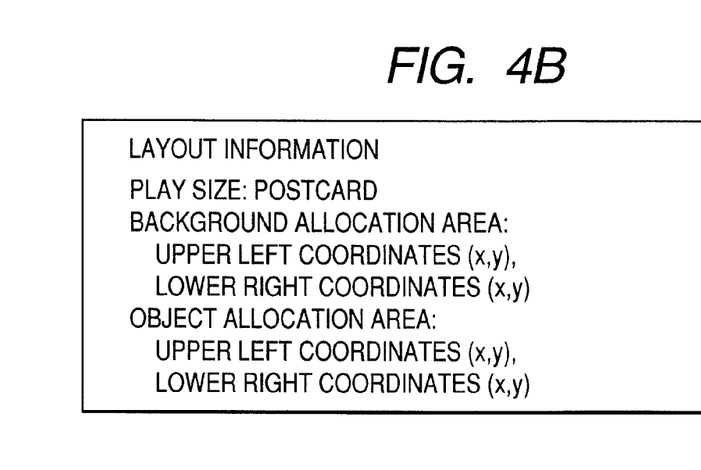

FIG. 4(A) is a schematic view showing background data stored in the removable memory 57. FIG. 4(B) is a schematic view showing layout information for defining the composite process of the background data and the object data. The layout information for defining the composite process of the background data and the object data are stored in the removable memory 57 to be correlated with the background data.

The background data and the layout information define the templates used to form printed matters such as a greeting card illustrated with a photograph, a seal illustrated with a photograph, etc., and are stored previously in the ROM 70 or the removable memory 57. Then, explanation will be made hereunder under the assumption that the background data and the layout information are stored in the removable memory 57. The background data represents an image 80 composed of a line drawing, painting all over, characters, etc. The hatched area may be defined by setting a value indicating a predetermined transparency, or the so-called α channel for defining which one of the background image and the object image should be displayed preferentially may be defined separately from the data that defines the background image. The background data and the layout information may be defined every standard size of the reproducing medium such as a printing paper, etc., otherwise one background data and one layout information may be defined for one design on a basis of a particular size respectively and then these information may be converted in response to a play size in the play mode.

The layout information are composed of data indicating the play size, the coordinates for defining a rectangular area in the play area corresponding to the play size to which the background data are allocated (object allocation area), the coordinates for defining a rectangular area in the play area to which the object data are allocated (object allocation area), and so forth.

In the printing system or the display system that synthesizes the background data and the object data by using the layout information to play synthesized data, the background data and the object data are expanded or contracted to respond to the background allocation area and the object allocation area and these expanded or contracted data are allocated to the background allocation area and the object allocation area. In the areas in which the background allocation area and the object allocation area are overlapped with each other, any one pixel of the background data or the object data is played preferentially.

Further, in the situation that the composite process of final outputs of the printing, or the like is not executed in the digital camera 1, but such composite process of final outputs of the printing, or the like is executed after the object data, the background data and the layout information are transferred to a personal computer or a stand-alone printer, true background data used to form the composite image data may be stored in the personal computer or the stand-alone printer and then the displaying process may be executed in the digital camera 1 by using the data that has a lower resolution and a rougher tone than the true background data. When doing this, a memory space in the digital camera 1 is by no means taken up by the background data and also the background data can be processed at a high speed.

Figure 5:
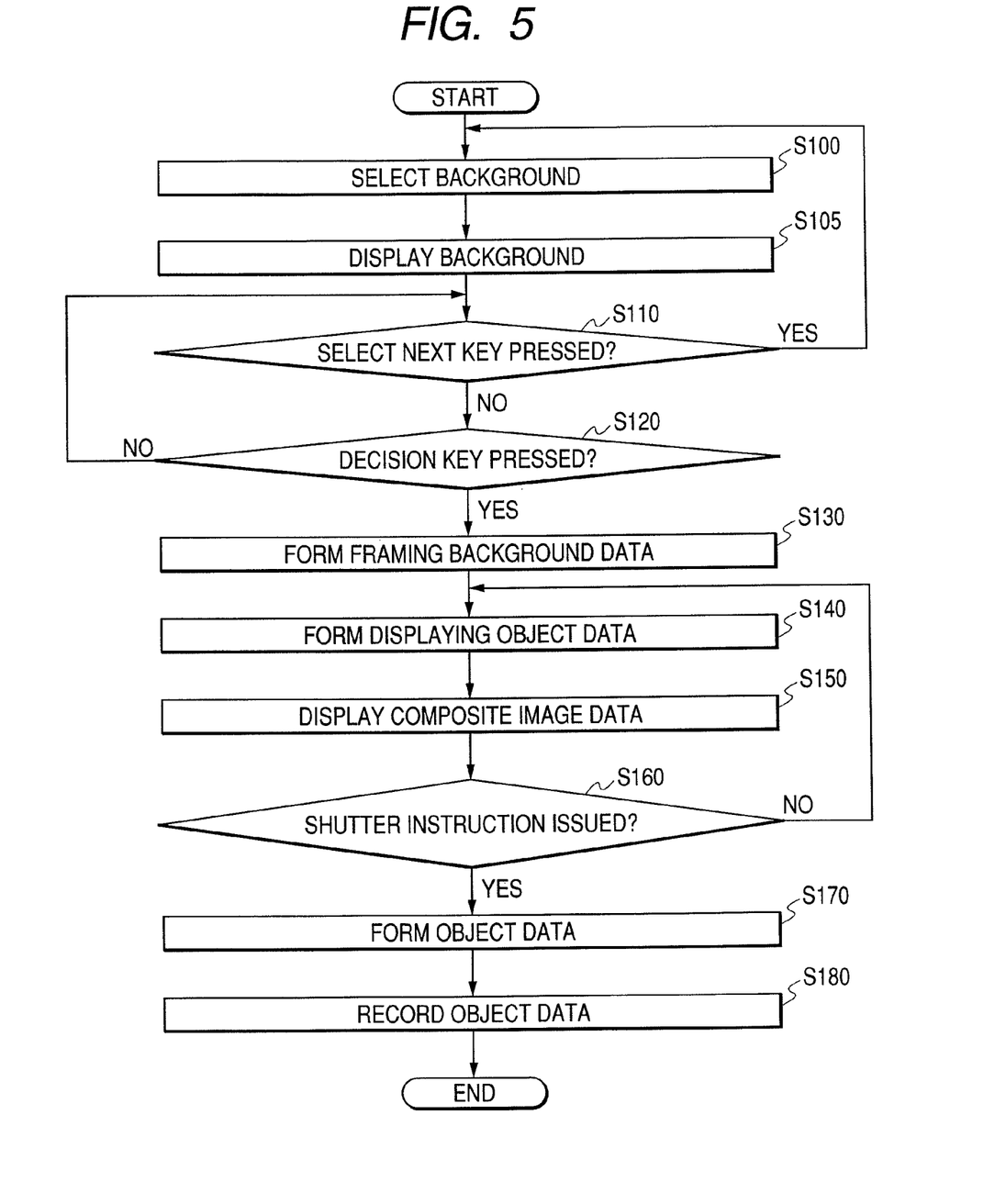
FIG. 5 is a flowchart showing a flow of processes of storing object data in the removable memory in the embodiment of the present invention.

The background data is explained as above. Next, an operation of the digital camera 1 will be explained hereunder. FIG. 5 is a flowchart showing a flow of processes of storing the object data in the removable memory 57. Sequences shown in FIG. 5 are started when the operator pushes the background setting button 18 in the shooting mode that is decided based on a rotation angle of the dial switch 16.

In step S100, any one of the background data stored in the removable memory 57 is selected. In step S105, the background data stored in the selected background data is displayed as follows. First, the background data is read from the removable memory 57 by the reader/writer 56, then expanded by the compression/expansion processing portion 54, and then stored in the RAM 66. In this case, explanation is made under the assumption that the background data is compressed in advance and recorded, but the background data may be recorded in its uncompressed state. Then, the background data is compressed in answer to the number of pixels in the display area of the LCD 26, and then the rotating process is applied as the case may be. Assumed that the number of pixels in the display area of the LCD 26 is set to 320×240 pixels and the background data has 640×960 pixels directed vertically, the displaying background data of 320×213 pixels is formed by thinning the number of pixels into ⅓ in vertical and horizontal directions and then rotating the resultant data by 90°. It is desired that, in order to simplify the hardware and deal with the background data having any number of pixels, this process should be executed according to a program executed by the CPU 68. Also, the displaying background data whose size is fitted to the display area of the LCD 26 may be recorded previously in the removable memory 57 and then displayed as it is. The displaying background data is stored in the frame buffer 62 and then displayed correspondingly when the display controlling portion 58 drives the LCD 26. When the select next key 20 is pressed in step S110, the process returns to step S100. Thus, the next background data is selected and foregoing processes are repeated.

Figure 6:
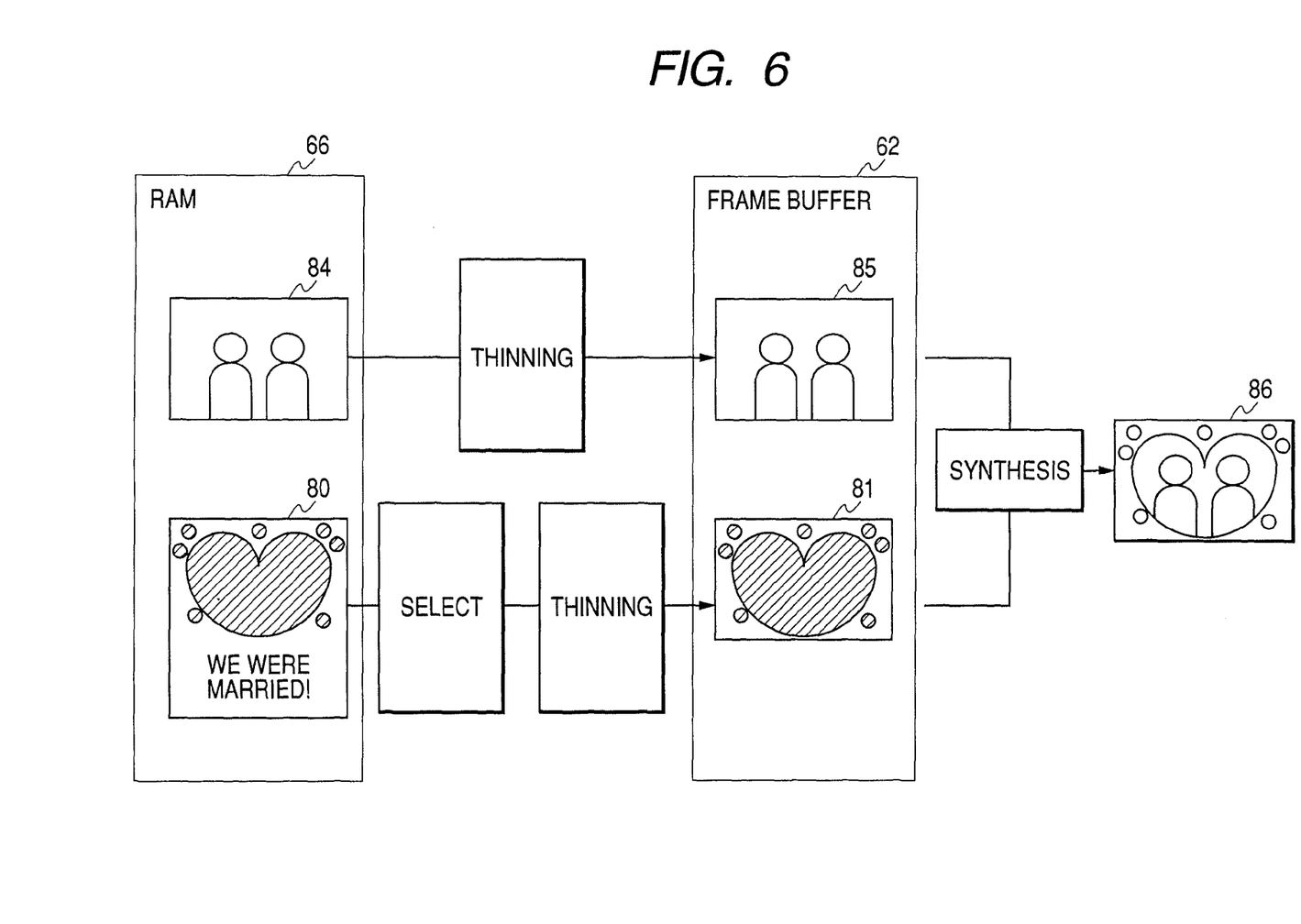
FIG. 6 is a schematic view explaining framing composite image data by the embodiment of the present invention.

When the decision key 24 is pressed in step S120, a part of the background data 80 stored in the RAM 66 in step S105 is stored in the foreground area of the frame buffer 62, as shown in FIG. 6, in step S130. More particularly, the area to be superposed on object data 84 is selected from the background data 80 and also a selected area of the object data 84 is stored in the foreground area of the LC frame buffer 62. In other words, the area to be superposed on object data 84 is selected from the background data 80, and also the selected area of the object data 84 that is thinned in accordance with the number of pixels in the display area of the LCD 26 and rotated as the case may be (framing background data 81) is stored in the foreground area of the frame buffer 62. That is, only the portion of the background data to be overlapped with the object data is stored in the foreground area of the frame buffer 62. It is desired that, in order to simplify the hardware and deal with the background data having any number of pixels, this process should be executed according to the program executed by the CPU 68. In this case, the data equivalent to the framing background data 81 may be recorded previously in the removable memory 57 and then displayed as it is.

Then, the object image is displayed as a moving picture in a transparent area of the background data by repeating S140, S150, described hereunder, until the shutter button 28 is pushed. In step S140, a predetermined control signal is input into the scanning controlling portion 76, the electric charges stored in the image sensor 44 for a predetermined time are scanned, the object data 84 formed by the digital image processing portion 52 is stored in the RAM 66 as shown in FIG. 6, and the object data 84 that is thinned in response to the number of pixels of the display area (displaying object data 85) is stored in the background area of the frame buffer 62. Since the thinning process mentioned herein is the process that is applied to all object data independent of whether the object data is to be synthesized with the background data or the object data is not to be synthesized with the background data, it is desired that such process should be executed at a high speed by using the hardware that is dedicatedly designed to permit the smooth display of the moving picture. If the process of contracting the object data in response to the display area of the LCD 26 is executed at a high speed by using the dedicatedly designed hardware, the object image can be displayed smoothly as the moving picture in the transparent area of the background data.

Figure 1A:
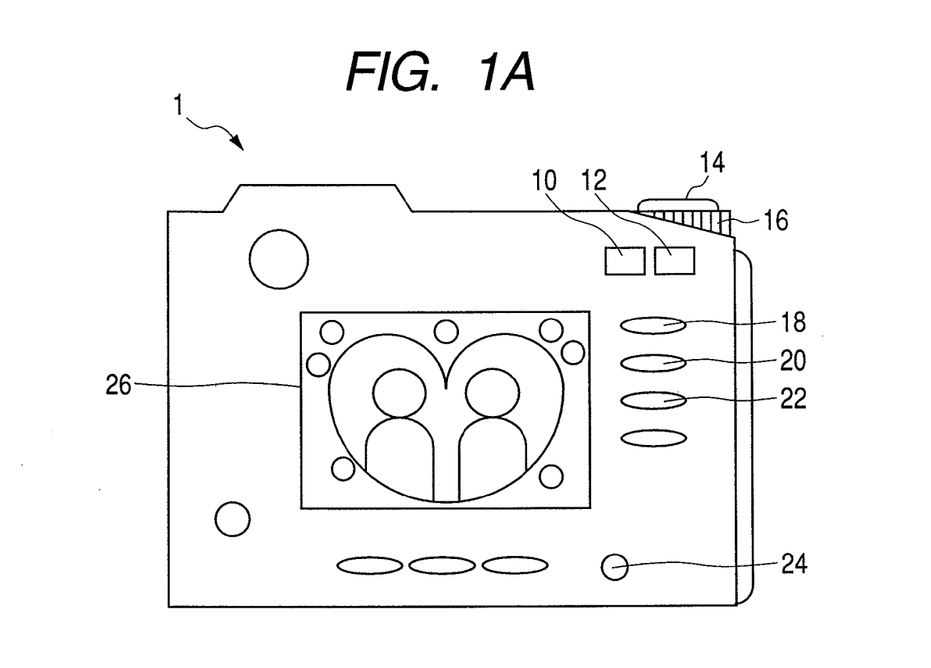
FIG. 1 is a rear view showing a digital camera according to an embodiment of the present invention, wherein (A) shows a shooting mode and (B) shows a play mode.

In step S150, the display controlling portion 58 synthesizes the displaying object data 85 stored in the background area of the frame buffer 62 and the framing background data 81 stored in the foreground area of the frame buffer 62 and outputs a driving signal to the LCD 26, and thus a framing composite image is displayed, as shown in FIG. 1(A). Concretely, for example, the driving signal is output to the LCD 26 based on the tone value of the target pixel of the displaying object data 82 if the tone value of the target pixel of the framing background data 81 is the tone value that is assigned previously to a transparent color (e.g., above R=00H, G=00H, B=00H), while the driving signal is output to the LCD 26 based on the tone value of the target pixel of the framing background data 81 in remaining cases. At this time, the data selected as a source of the driving signal being output to the LCD 26 are framing composite image data 86, which correspond to composite image data set forth in claims.

Figure 7A:
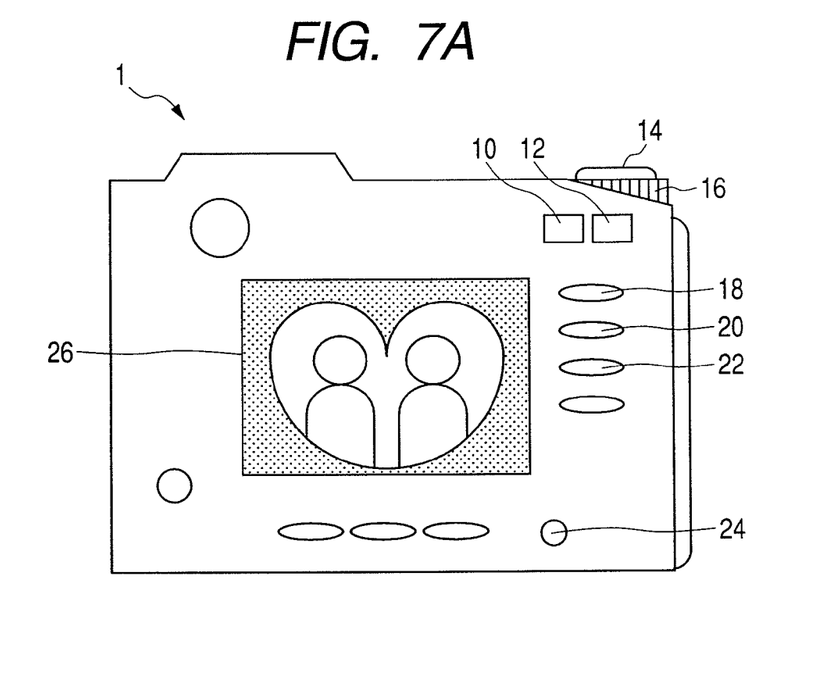
FIG. 7 is a rear view showing the digital camera on which the framing composite image data by the embodiment of the present invention is displayed.
Figure 7B:
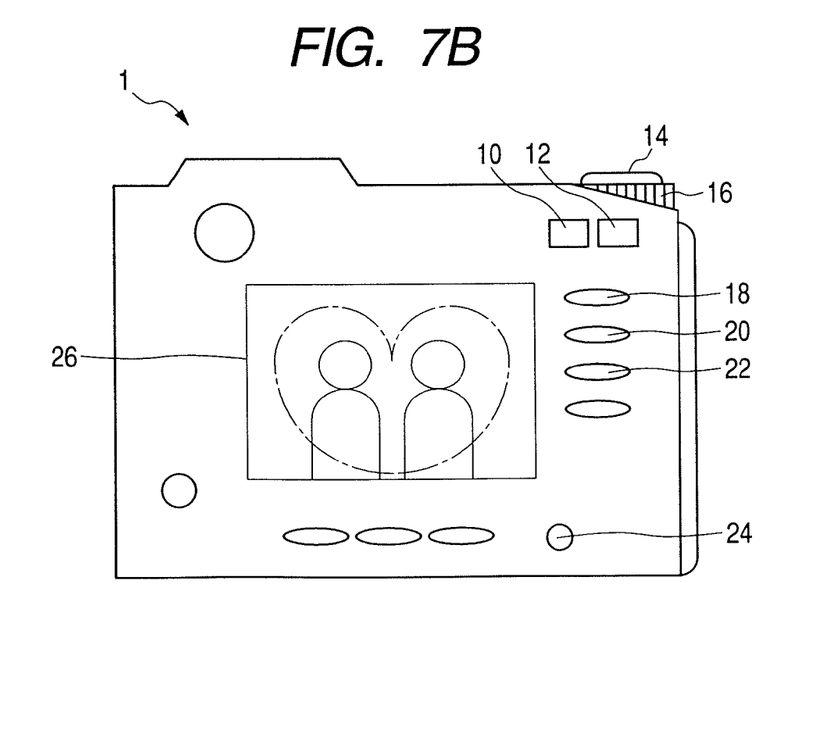

Here, it becomes ready to mate the object image with the background image by displaying a part of the background image data on the LCD 26, as shown in FIG. 1(A). In this event, if the operator can discriminate at least a profile of the area that is synthesized with the foreground of the background data, such operator can push the shutter button 28 in an appropriate composition. For this reason, for example, as shown in FIG. 7(A), the object image may be displayed as the moving picture. In the example shown in FIG. 7(A), the background data is not displayed and the object is displayed as the moving picture only in the area that is synthesized with the foreground of the background data, and the object is not displayed in remaining areas. Also, as shown in FIG. 7(B), the overall object data may be displayed but the background data may not be displayed, and then a line taken along the profile of the area that is synthesized with the foreground of the background data may be displayed in predetermined color to overlap with the object data.

In step S160, it is decided whether or not a shutter instruction is input, i.e., whether or not the shutter button 28 is pushed. If it is not decided that the shutter button 28 is pushed, the process goes back to step S130 and above processes are repeated. In step S160, if it is decided that the shutter button 28 is pushed, the process goes to step S170.

In step S170, like step S130, the predetermined control signal is input into the scanning controlling portion 76, the electric charges stored in the image sensor 44 for a predetermined time are scanned, the object data is formed by the digital image processing portion 52, and the object data is stored in the RAM 66.

In step S180, the compressed image data is formed by compressing the object data stored in the RAM 66 by means of the compression/expansion processing portion 54, and then such data is stored in the removable memory 57 by the reader/writer 56. Also, in step S180, data to correlate the object data recorded at this time with the background data selected by pressing the decision key 24 in step S110 is stored in the removable memory 57. Since the data obtained by synthesizing the background data and the object data is not stored in the removable memory 57 but the object data itself is stored in the removable memory 57 as it is, the background can be changed, erased, etc. after the shooting.

Figure 8:
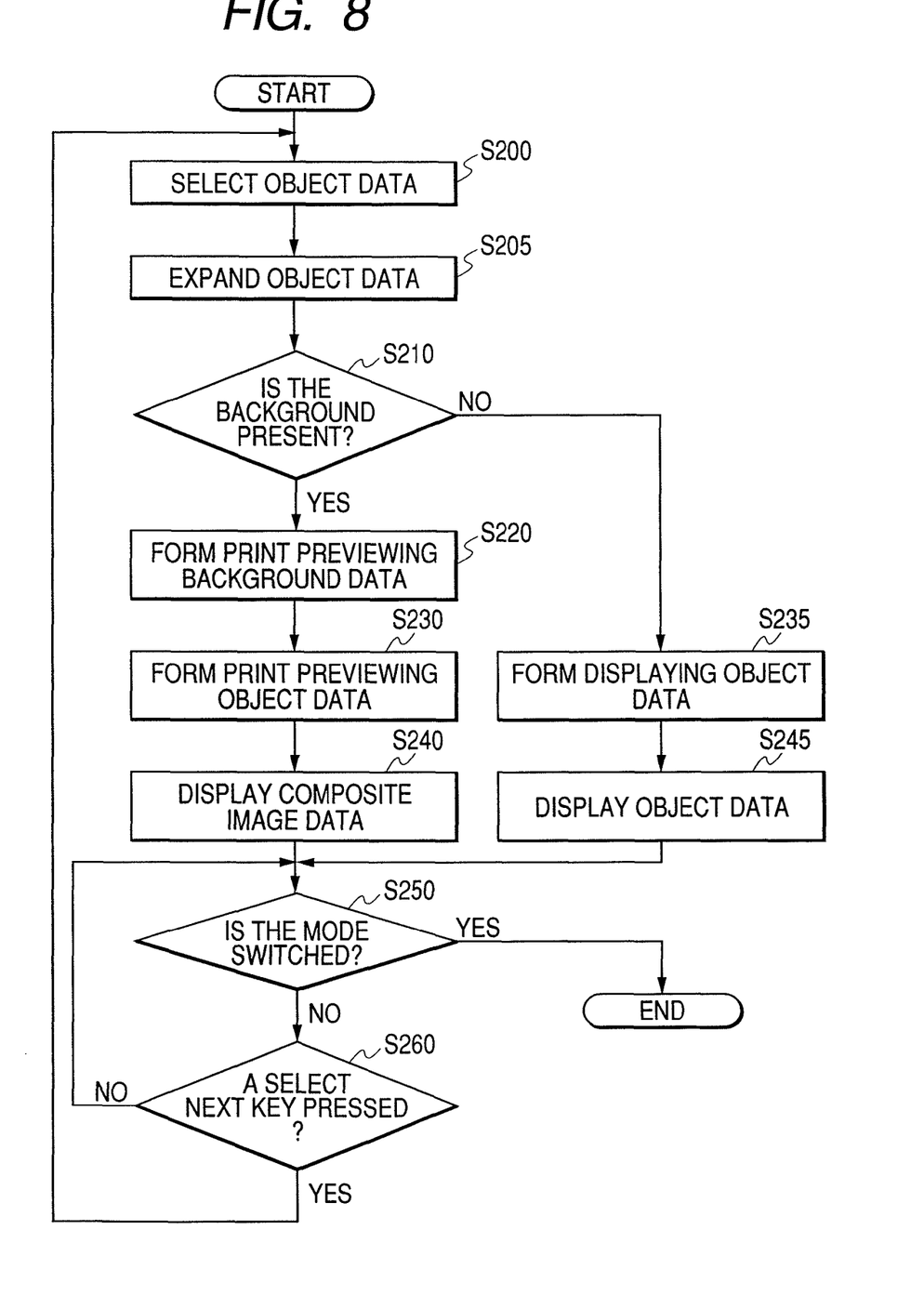
FIG. 8 is a flowchart showing a flow of processes of playing the object data stored in the removable memory in the embodiment of the present invention.

With the above, a flow of process of storing the object data in the removable memory 57 is explained. Next, a process of playing the object data stored in the removable memory 57 will be explained hereunder. FIG. 8 is a flowchart showing a flow of the process of playing the object data stored in the removable memory 57. Sequences shown in FIG. 8 are started when a rotation angle of the dial switch corresponding to a play mode is sensed by the operating portion 64.

In step S200, any one of the object data stored in the removable memory 57 is selected. In step S205, the selected object data is read from the removable memory 57 by the reader/writer 56, then expanded by the compression/expansion processing portion, and then stored in the RAM 66. In this case, explanation is made under the assumption that the object data is previously compressed and recorded, but such data may be recorded in its uncompressed state. In step S210, it is decided whether or not the background data is correlated with the selected object data. The process goes to step S235 et seq. to display the object data as a single body if they are not correlated mutually, the process goes to step S220 et seq. to display the composite image of the object data and the background data if they are correlated mutually.

Figure 9:
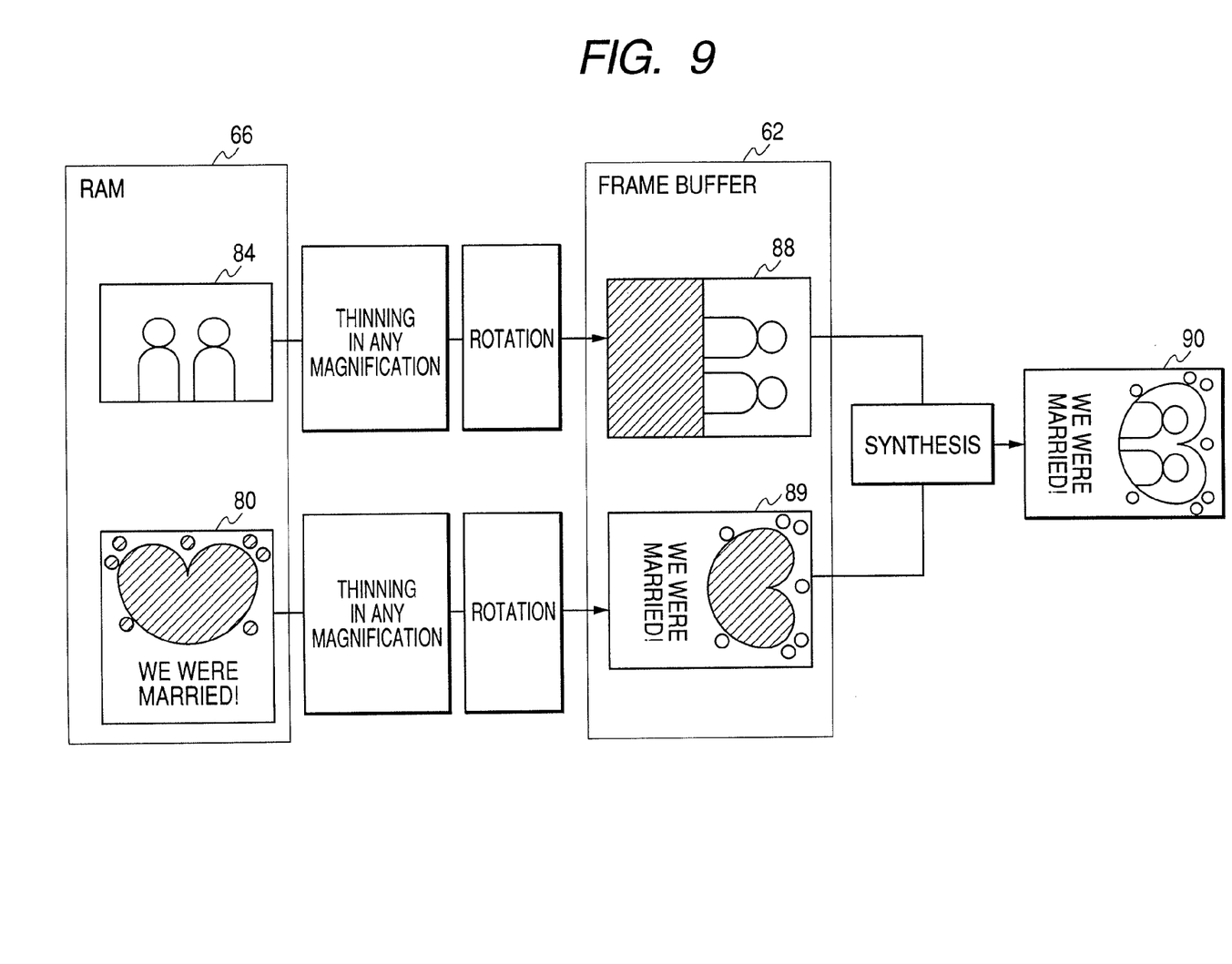
FIG. 9 is a schematic view explaining print previewing composite image data by the embodiment of the present invention is displayed.

In step S220, print previewing background data is formed from the background data that is correlated with the object data selected in step S200. More particularly, first the background data is read from the removable memory 57 by the reader/writer 56 and then expanded by the compression/expansion processing portion 54, and then the background data 80 is stored in the RAM 66, as shown in FIG. 9. Then, in order to display the overall background data the number of pixels of which is larger than the display area on one screen, a contracting process to respond to the number of pixels of the background data and a rotation process at need are carried out. For example, suppose that the display area is set to 320×240 pixels and the background data 80 has 640×960 pixels directed vertically, the print previewing background data 89 of 320×213 pixels is formed by thinning the number of pixels of the background data 80 into ⅓ in vertical and horizontal directions and then rotating the resultant data by 90°, and then stored in the foreground area of the frame buffer 62. It is desired that, in order to simplify the hardware and set a magnification of the thinning process arbitrarily so as to deal with the background data having any number of pixels, this process should be executed according to a program executed by the CPU 68. Also, the print previewing background data whose size is fitted to the display area of the LCD 26 may be recorded previously in the removable memory 57 and then displayed as it is.

In step S230, as shown in FIG. 9, print previewing object data is formed by thinning the object data stored in the RAM 66 in response to the object allocation area, which is defined by the layout information correlated with the background data, and then applying the rotation, etc. as the case may be. At this time, if the number of pixels in the area that is derived by converting the object allocation area defined by the layout information in response to the display area of the LCD 26 is smaller than the number of pixels in the display area of the LCD 26, the thinning process executed in the play mode in step S230 has a smaller magnification than the thinning process executed in the shooting mode in step S140. In the event that the background allocation area and the object allocation area defined by the layout information are translated in response to the display area of the LCD 26, if the background allocation area is set to correspond to the overall display area of the LCD 26, the object allocation area becomes smaller than the display area of the LCD 26 when such object allocation area is smaller than the background allocation area. In this case, in the event that the background allocation area and the object allocation area defined by the layout information are translated in response to the display area of the LCD 26, these areas may be translated in such a manner that a play size is set to correspond to the overall display area of the LCD 26. Also, print previewing layout information used to synthesize the object data with the print previewing background data and display the synthesized data may be recorded previously in the removable memory 57 separately from the layout information for final outputs of the printing, or the like. Also, for example, as shown in FIG. 9, when the object data directed vertically is synthesized with the print previewing background data 89, the object data 84 stored horizontally in the RAM 66 may be rotated clockwise by 90°.

In the example shown in FIG. 9, print previewing object data 88 of 160×213 pixels and directed vertically is formed from the object data 84 of 640×480 pixels and directed horizontally and stored in the RAM 66. The print previewing object data 88 is stored in an area, which corresponds to the right side of a screen, out of the foreground area of the frame buffer 62, while a value indicating a transparency is stored in an area which corresponds to the left side of the screen. It is desired that, in order to simplify the hardware and set a magnification of the thinning process arbitrarily so as to deal with the background data having any number of pixels, the process in step S230 should be executed according to the program executed by the CPU 68.

Figure 1B:
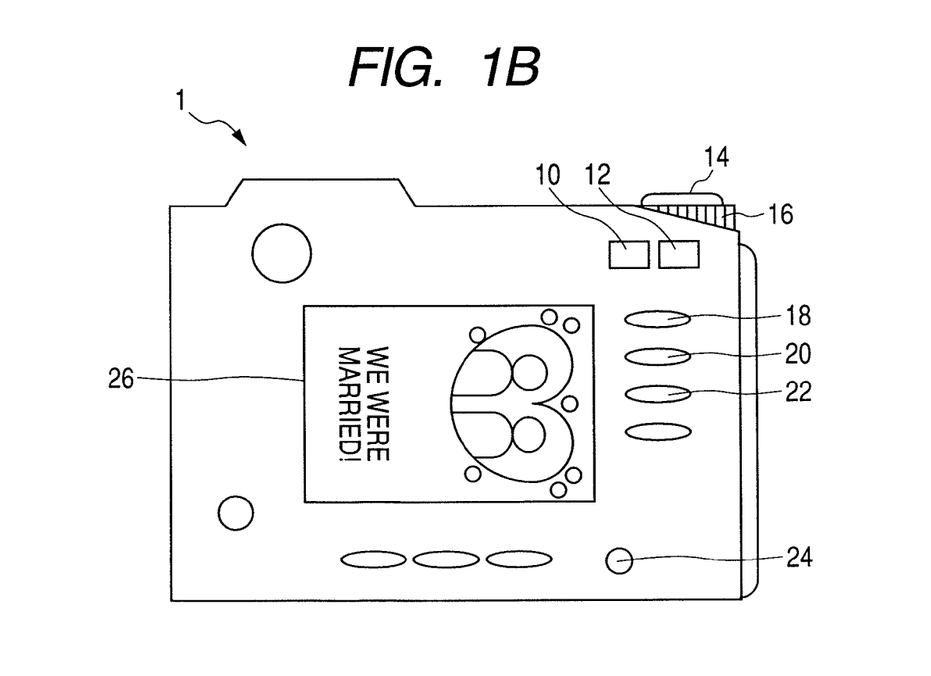

In step S240, overall print previewing composite image is displayed on one screen, as shown in FIG. 1(B), when the display controlling portion 58 synthesizes the print previewing object data 88 and the print previewing background data 89 stored in the frame buffer 62 and outputs the driving signal to the LCD 26. More concretely, for example, if it is found by scanning preferentially the print previewing background data 89 stored in the frame buffer 62 that the tone value of the target pixel of the print previewing background data 89 corresponds to the tone value assigned in advance to a transparent color (e.g., above-mentioned R=00H, G=00H, B=00H), the drive signal is output to the LCD 26 based on the tone value of the target pixel of the print previewing object data 88. While, the drive signal is output to the LCD 26 based on the tone value of the target pixel of the print previewing background data 89 in remaining cases. The data selected as a source of the drive signal being output to the LCD 26 at this time corresponds to print previewing composite image data 90, which is equivalent to composite image data set forth in claims.

In step S245, the object data with which the background data is not correlated is displayed as follows. The display controlling portion 58 thins the object data in response to the number of pixels of the display area of the LCD 26 and stores in the frame buffer 62. Suppose that the number of pixels of the display area is 320×240 pixels and the object data is 640×480 pixels, the number of pixels of the object data is thinned to ½ in vertical and horizontal directions and such object data is stored in the frame buffer 62. The object data stored in the frame buffer 62 is displayed as shown in FIG. 3(A) when the display controlling portion 58 drives the LCD 26 correspondingly.

In step S250, it is decided whether or not a mode switching instruction is input, i.e., whether or not a rotation angle of the dial switch 16 is changed. Then, if the mode switching instruction is input, the play mode is ended and the mode is switched to another mode. If the mode switching instruction is not input, the mode switching instruction and pressing of the select next key 20 are repeatedly detected until the pressing of the select next key 20 is detected in step S260. If the pressing of the select next key 20 is detected in step S260, the process goes back to step S200 wherein the next object data is selected and above processes are repeated.

In the embodiment of the present invention, a synthesizing means set forth in claims is composed of the display controlling portion 58, the frame buffer 62, etc. and a function thereof is implemented by the processes in step S150, step S240, etc. A magnification varying process set forth in claims corresponds to the process in step S230. A playing means set forth in claims is composed of the CPU 68, the display controlling portion 58, the frame buffer 62, etc. and a function thereof is implemented by the processes in step S230, step S240, etc. An image processing means set forth in claims is composed of the CDS circuit 46, the AGC circuit 48, the A/D converter 50, the digital image processing portion 52, etc. and a function thereof is implemented by the processes in step S140 and step S170. A setting means set forth in claims is composed of the background setting button 18, the select next key 20, the select previous key 22, the decision key 24, etc. and a function thereof is implemented by the processes in steps S100, S105, S110 and S120. A framing assisting means set forth in claims is composed of the CPU 68, the display controlling portion 58, the frame buffer 62, etc. and a function thereof is implemented by the processes in step S130, step S140, and step S150. A recording means set forth in claims is composed of the CPU 68, the compression/expansion processing portion 54, the reader/writer 56, etc. and a function thereof is implemented by the process in step S180.

In the embodiment of the present invention described as above, the object data of 640×480 pixels is contracted into 320×240 pixels and displayed together with a part of the background in the shooting mode, as shown in FIG. 1(A), whereas the object data of 640×480 pixels is contracted into 160×213 pixels and a part of resultant data is displayed together with the entirety of the background in the play mode, as shown in FIG. 1(B). In other words, when the object is displayed as a moving picture together with a profile of the area synthesized with the foreground of the background data in the shooting mode, the object image is displayed largely as a moving picture by displaying the framing composite image data that corresponds to a portion having the same size as the number of pixels of the object data out of the printing composite image data. Therefore, the operator can take a picture while checking details of the object image. Also, in the shooting mode, it is easy for the operator to take a picture in the composition such that a pertinent portion (e.g., face) of the object is inserted into the area that is not trimmed by the composite process since a profile of the area of the object data that is synthesized with the foreground of the background data is displayed. Therefore, according to the above embodiment, it is easy to record the image data used in the composite process in the adequate composition.

Also, in the above embodiment, since the object data and the background data are displayed in the play mode in a smaller magnification than the shooting mode, the entirety of the print previewing composite image data 90 corresponding to the printing composite image data can be displayed on one screen. Therefore, it is easy to grasp the printing image of the composite image.

Also, in the above embodiment, the background and the foreground are set in the frame buffer 62 and the composite process itself is carried out in the display controlling portion 58. In this case, the composite image data obtained by synthesizing the background data and the object data by causing the CPU 68 to execute the composite process in compliance with the program may be stored in the frame buffer 62, and then the composite image data formed by using the CPU 68 may be output as it is without the composite process in the display controlling portion 58.

The invention claimed is:

1. An apparatus comprising:
an obtaining unit which obtains a first image and information about a part of the first image from a storing unit;
a generating unit which generates a second image from output of an image sensor;
a synthesizing unit which synthesizes the second image with the part of the first image based on the information to generate a synthesized image in which the part of the first image is superposed on the second image; and
a displaying unit which displays a first part of the synthesized image without displaying a second part of the synthesized image, the first part of the synthesized image including all parts of the second image that were not superposed by the part of the first image in generating the synthesized image, and the second part of the synthesized image including the part of the first image.

2. The apparatus according to claim 1, wherein:
the second image is stored in the storing unit in response to an instruction of a user, and
the second image is correlated with the first image.

3. The apparatus according to claim 1, wherein the synthesized image is output.

4. The apparatus according to claim 1, wherein the displaying unit displays the first part of the synthesized image based on the information.

5. A non-transitory computer-readable recording medium in which a computer program causing a computer to execute a method is recorded, the method comprising:
obtaining a first image and information about a part of the first image from a storing unit;
generating a second image from an output of an image sensor;
synthesizing the second image with the part of the first image based on the information to generate a synthesized image in which the part of the first image is superposed on and the second image; and
displaying a first part of the synthesized image without displaying a second part of the synthesized image, the first part of the synthesized image including all parts of the second image are synthesized, that were not superposed by the part of the first image in generating the synthesized image, and the second part of the synthesized image including the part of the first image.

6. The computer-readable recording medium according to claim 5, wherein the first part of the synthesized image is displayed based on the information.

7. An apparatus comprising:
an obtaining unit which obtains a first image from a storing unit;
a generating unit which generates a second image from output of an image sensor;
a synthesizing unit which synthesizes the second image with a part of the first image to generate a synthesized image in which the part of the first image is superposed on the second image; and
a displaying unit which displays a first part of the synthesized image without displaying a second part of the synthesized image, the first part of the synthesized image corresponding to a all positions of the second image that were not superposed by the part of the first image in generating the synthesized image, and the second part of the synthesized image corresponding to a position of the part of the first image.

8. The apparatus according to claim 7, wherein the displaying unit displays the first part of the synthesized image based on information obtained from the storing unit.

9. An apparatus comprising:
an obtaining unit which obtains a framing image and layout information about a part of the framing image from a storing unit;
a generating unit which generates an object image using output from an image sensor;
a synthesizing unit which synthesizes the object image with the part of the framing image based on the layout information to generate a synthesized image in which the part of the framing image is superposed on the object image; and
a displaying unit which displays a first part of the synthesized image without displaying a second part of the synthesized image, the first part of the synthesized image including all parts of the object image that were not superposed by the part of the framing image in generating the synthesized image, and the second part of the synthesized image including the part of the framing image.

* * * * *

UNITED STATES PATENT AND TRADEMARK OFFICE
CERTIFICATE OF CORRECTION

PATENT NO. : 8,120,791 B2
APPLICATION NO. : 12/494820
DATED : February 21, 2012
INVENTOR(S) : Masanobu Shirakawa and Shuji Tsuji Page 1 of 1

It is certified that error appears in the above-identified patent and that said Letters Patent is hereby corrected as shown below:

Related U.S. Application Data should read:
(63) Continuation of application No. 10/965,858, filed on Oct. 18, 2004, now Pat. No. 7,573,601, which is a continuation of application No. PCT/JP03/04948, filed on Apr. 17, 2003.

Signed and Sealed this
Thirty-first Day of July, 2012

David J. Kappos
*Director of the United States Patent and Trademark Office*